United States Patent [19]

Gadow et al.

[11] Patent Number: 4,657,873

[45] Date of Patent: Apr. 14, 1987

[54] PREACTIVATED PLASTICS SURFACES FOR IMMOBILIZING ORGANO-CHEMICAL AND BIOLOGIC MATERIALS

[75] Inventors: André Gadow, Lubeck; W. Graham Wood, Gross-Grönau, both of Fed. Rep. of Germany

[73] Assignee: Henning Berlin GmbH, Berlin, Fed. Rep. of Germany

[21] Appl. No.: 635,224

[22] Filed: Jul. 27, 1984

[30] Foreign Application Priority Data

Jul. 29, 1983 [DE] Fed. Rep. of Germany ....... 3327327
Nov. 8, 1983 [EP] European Pat. Off. ........ 83111144.8

[51] Int. Cl.$^4$ .......................................... G01N 33/549
[52] U.S. Cl. ........................................ 436/532; 435/7;
435/180; 435/181; 436/500; 436/531
[58] Field of Search ............................ 435/181, 180, 7;
436/532, 531, 500

[56] References Cited

U.S. PATENT DOCUMENTS 4,525,465  6/1985  Someno et al. ..................... 435/181

*Primary Examiner*—Sam Rosen
*Attorney, Agent, or Firm*—Wegner & Bretschneider

[57] ABSTRACT

Plastics surfaces are preactivated for immobilizing organo-chemical and biologic materials by coating the surfaces with a polypeptide which consists of a defined composition of hydrophobic amino acids and amino acids having side chains capable of activation and coupling. After activation of the plastics surfaces having been coated in this manner with various coupling reagents, it is possible to firmly fix organo-chemical and biologic materials. The materials having been immobilized in this manner are extremely stable to various reaction conditions.

9 Claims, No Drawings

PREACTIVATED PLASTICS SURFACES FOR IMMOBILIZING ORGANO-CHEMICAL AND BIOLOGIC MATERIALS

It is an object of the present invention to provide preactivated plastics surfaces for immobilizing organo-chemical and biologic materials such as antigens, antibodies, allergens, tissues, enzymes, cofactors, etc. It is another object of this invention to provide a process of preparing such preactivated plastics surfaces and their use.

In many immunological, histological and enzymatic methods, it is necessary and, for simplifying the process, advantageous and desirable to immobilize corresponding components of the test on solid carriers. Immobilized antibodies and antigens are used in many cases in radio, enzyme, fluorescence and luminescence immunoassays. Immobilized tissue is used in histological tests. Allergens (e.g., birch pollen, etc.) immobilized on paper discs are used in what is known as the RAST test (radio-allergo-sorbent test) for diagnosing antibodies to allergens. Immobilized enzymes are used, for example, in what is known as enzyme reactors, but also immobilized enzyme substrates and cofactors fixed to solid carriers are used in enzymatic tests. Immobilization may be effected on various solid phases such as glass, plastics or other homogeneous solids using either the vessel wall (tubes or microtiter plates) or the surface of micro- and macroparticles (grains, balls, little discs, etc.). A favorite solid phase for the immobilization of various organo-chemical and biologic materials is polystyrene, it being possible in this case that the coupling may be effected to micro- and macroparticles.

For a better reproducible immobilization of specific antibodies, these were covalently bound to poly-L-lysine which in turn was adsorbed on polystyrene balls. In addition to poly-L-lysine, other polyamines such as poly-L-arginines, poly-L-histidines or poly-L-ornithines have also been investigated, best values having been achieved with poly-lysine; see Maija Leinonen and Carl E. Frasch, Infection and Immunity, 1982, pp. 1203–1207, and Barry M. Gray, Journal of Immunological Methods, 28 (1979), pp. 187–192.

All of the plastics surfaces having been investigated up to this time for immobilizing antibodies or antigens still exhibit considerable disadvantages because they lead either to non-reproducible values or to undesirable, difficulty controllable wash-out reactions or non-specific alterations of the antibodies or antigens.

It is an object of the invention to provide the preactivation of plastics surfaces by a process which is suitable to immobilize organo-chemical and biologic materials firmly and reproducibly on plastics without the known disadvantages of processes which exist up to this time. Extensive studies with respect to the optimization of the properties while considering various parameters such as temperature, reaction time, pH, and buffer system led to the surprising result that this object can be accomplished by plastics surfaces which are coated with a polypeptide which consists of a defined composition of hydrophobic amino acids such as phenylalanine, valine, leucine, etc. and of amino acids having side chains which bear groups capable of activation and coupling (lysine, arginine, ornithine, cysteine, glutamic acid, aspartic acid, etc.). Thus, typical representatives of these substances are polypeptides such as poly-phenylalanine-lysine, polyphenylalanine-glutamic acid, poly-leucine-lysine, poly-valine-cysteine, etc. Particularly preferred are phenylalanine-lysine copolymers.

The coating may be effected in accordance with the invention by treating the plastics surfaces with a solution or suspension of the polypeptide followed by washing them. This may then be followed by an activation step and the coupling.

The phenyl-lysine copolymer used has preferably a molar ratio of phenylalanine to lysine of 1:1. However, polymers having different ratios (2:1, 1:2, etc.) may also be used successfully on principle.

The molecular weight of the polypeptides should preferably be higher than 10,000. Outstandingly suited are polypeptides having a molecular weight of 30,000 to more than 200,000.

Polypeptides of this kind are already commercially available and are offered, for example, by the firms Miles-Yeda Ltd. (Kiryat Weizmann Rehovot, Israel) or SIGMA Chemie GmbH, Munich (Germany). Low molecular weight polypeptides are generally readily water-soluble; higher molecular weight ones are generally water-soluble or still well suspendable in the presence of heat.

The preactivatable plastics surfaces are contacted with such solutions or suspensions preferably at room temperature or refrigerator temperature for some hours, followed by washing. The plastics surfaces are coated thereby with an almost constant thin layer of the polypeptide. The hydrophobic portions of the polypeptide (in case of poly-phenylalanine-lysine, this is the phenylalanine portion) are thereby added to or deposited directly on the plastics surfaces, and the portions bearing the activatable groups (thus, for example, the lysine side chains with the terminal amino groups) which are hydrophilic and in most cases extend outwardly. These groups may be activated through reactions, a great number of which are described in literature, and the coupling of the organo-chemical and biologic materials may be directly effected subsequently to this activation. The activation which is necessary before the coupling may, for example, be effected by means of coupling reagents.

Coupling reagents which are suitable for the activation include, for example, for the direct coupling glutardialdehyde, cyanogen bromide, hydrazines, bisepoxiranes, divinyl sulfones, epichlorohydrin, benzoquinones, trichloro-s-triazines, isothiocyanates, aryl amines and phenyl hydrazines. The bonding types thereby formed include, for example, Michael adducts and Schiff bases, cyanate esters, triazinyles, ethers, imidocarbonates, amides, mixed anhydrides, alkylamines, esters. For the indirect coupling may be used reagents such as EEDQ (N-ethoxycarbonyl-2-ethoxy-1,2-dihydroquinoline), carbodiimides such as dicyclohexylcarbodiimide, 1-cyclohexyl-3-(2-morpholinyl-(4)-ethyl)-carbodiimide-m-ethyl-p-toluene-sulfonate, 1-ethyl-3-(3-dimethylaminopropyl)carbodiimide hydrochloride and N-hydroxysuccinimides. Further suitable reagents are heterobifunctional reagents such as MBS (m-maleimidobenzoyl-N-hydroxysuccinimide ester) and others.

Comparative studies with other preactivated surfaces had the result that organo-chemical and biologic materials having been immobilized in accordance with the invention are fixed to the surface particularly firmly and, above all, with excellent precision and reproducibility without the non-specific reactions and wash-out phenomena during later process steps which are known in the existing processes being encountered. The use of so-called detergents such as Tween 20 (polyoxyethylenesorbitan-monolaurate) and Triton X 100 (polyethylene ether) for readily washing away components which are fixed non-specifically in later process steps is possible without removing the specifically coupled portions. This was not possible in the existing purely adsorptive immobilization processes with the use of, for example, polystyrene. These advantages have been observed in case of a great variety of organo-chemical and biologic materials have been immobilized in accordance with the invention so that plastics surfaces having been preactivated in accordance with the invention may be used in various fields of application.

Therefore, phenylalanine-lysine copolymers are members of a class of substances which, due to its properties, may quite generally be used for the preactivation of plastics surfaces to which components which are capable of coupling such as antigens, antibodies, allergens, tissues, enzymes, substrates, cofactors, etc., are to be fixed. The preactivation acts reliably and unchangeably independently of which reagents are used to effect the final coupling of the material to be immobilized.

These surprisingly good properties in the preactivation of polystyrene balls with phenylalanine-lysine co-polymers, activation by means of glutardialdehyde and immobilization of antibodies were observed for the first time. It has been found that this is a general and widely and broadly applicable principle. Suitable plastics include substantially all of the hydrophobic plastics such as polystyrene, polyethylene, polypropylene, etc.

The examples which follow illustrate in greater detail plastics surfaces having been preactivated in accordance with the invention as well as processes for the preparation thereof and of the coupling of various materials.

EXAMPLE 1

(a) Immobilization After Preactivation 5 mg. of polyphenylalanine-lysine obtained from Sigma (MG 40 KD) or Miles-Yeda (MD 30 KD) are dissolved in a total of 200 ml of demineralized water while slightly heating and case onto 1000 polystyrene balls (Precision Plastic Ball Co., Chicago Ill.) having a diameter of 6.4 mm. The balls are allowed to stand for about 30 minutes at room temperature while occasionally gently shaking and then for 24 hrs. at refrigerator temperature (4° C.). The balls are then washed once by covering with a layer of a 0.15 moles/l saline solution and twice with demineralized water. The polystyrene balls having been coated in this manner may now be reacted directly with a coupling reagent, for example, with 0.5 percent by volume of pentane-1,5-dial (glutardialdehyde) in demineralized water for 30 minutes at room temperature. After the last-mentioned activation step, organo-chemical and biologic materials bearing amino groups may be directly coupled. Amounts of 1 to 5 $\mu g$ per polystyrene ball are generally obtained.

(b) Comparative Studies

Tables 1 and 2 show the stability and bonding properties of $T_4$ (thyroxin) as well as antibodies immobilized according to Example 1(a) against h-TSH (thyrotropin) and compare them with the properties of a conventional immobilization. Comparative review fo the immobilization of radioactively labelled $^{125}I$-$T_4$ (thyroxin) to polystyrene balls (a) purely adsorptively,
(b) after treatment of the polystyrene balls with glutardialdehyde and
(c) after coating according to the invention with phenylalanine-lysine copolymer followed by activation with glutardialdehyde.

Coupling time, 38 hrs. at 4° C.; $^{125}I$-$T_4$ dissolved in 0.01 moles/l of phosphate buffer pH 8.5 was offered in excess.

TABLE 1

| Kind of activation of the polystyrene balls | Quantity fixed per ball after washing with | | |
|---|---|---|---|
| | 0.15 moles/l. of NaCl | 0.1% by vol. of Tween 20 | 5% by volume of KCl |
| (a) exclusively by adsorption | *3688 cpm ±669 | 513 cpm ±54 | 973 cpm ±109 |
| (b) only with glutardialdehyde | 3097 cpm ±366 | 344 cpm ±110 | 1196 cpm ±112 |
| (c) according to Example 1(a) | 15615 cpm ±254 | 10233 cpm ±333 | 10585 cpm ±695 |

*The variance mentioned above relates in each case to 10 measured samples (cpm = counts per minute).

Comparative review of the bonding of radioactively marked 125 $^{125}I$-TSH (human thyrotropin) to antibodies against human thyrotropin having been bonded under optimum conditions to polystyrene balls (a) purely adsorptively,
(b) after treatment of the polystyrene balls with glutardialdehyde and
(c) after coating according to the invention with phenylalanine-lysine copolymer followed by activation with glutardialdehyde.

There is shown the ratio of the specific and non-specific binding to the offered total activity after a reaction time of 6 hrs. at room temperature. Radioactively labelled $^{125}I$-TBG (thyroxin-binding globulin) was used for measuring the non-specific binding.

TABLE 2

| Kind of activation of the polystyrene balls | Ratio Bo/T, UB/T after washing with | | | | | |
|---|---|---|---|---|---|---|
| | 0.15 moles/l. NaCl | | 0.1% by volume Tween 20 | | 5% by volume KCl | |
| | (Bo/T) × 100 | (UB/T) × 100 | (Bo/T) × 100 | (UB/T) × 100 | (Bo/T) × 100 | (UB/T) × 100 |
| (a) exclusively by adsorption | 57 ± 2* | 2 | 19 ± 0.7 | 2 | 35 ± 0.6 | 2 |
| (b) only with glutardialdehyde | 11 ± 1 | 4 | 6 ± 0.5 | 3 | 12 ± 0.2 | 4 |
| (c) according to Example 1(a) | 44 ± 0.6 | 4 | 39 ± 0.4 | 3 | 39 ± 0.2 | 5 |

T = total activity; Bo = specific binding; UB = non-specific binding.
*The variance shown relates in each case to 10 measured samples.

EXAMPLE 2

Polystyrene tubes are filled with the same solution as in Example 1, allowed to stand overnight and flushed once with 0.15 moles/l of NaCl in demineralized $H_2O$ and twice with demineralized water. The tubes having been treated in this manner are filled with the pentane-1,5-dial solution described in Example 1, allowed to react for 30 minutes at room temperature and correspondingly washed. The tubes having been treated in this manner are directly suited thereafter to firmly bond organo-chemical and biologic materials with amino groups capable of coupling.

EXAMPLE 3

The individual recesses in a microtiter plate are filled with the solution described in Example 1 and further treated as described in Example 2. The plate fixes biologic material.

EXAMPLE 4

100 g of polystyrene in the form of microparticles (Dow-Latex Serva) are overcoated with the solution described in Example 1. The further reaction is effected in an analogous manner. Filtration is effected for washing.

Activation with glutardialdehyde followed by coupling of amino group-bearing substances results in the formation of Schiff bases which may be reduced with the use of sodium borohydride or sodium cyanoborohydride. The coating according to the invention resists such treatments without detriment.

EXAMPLE 5

Tubes of polyethylene and polypropylene are preactivated in the manner described in Example 2. The tubes having been treated in this manner are suitable in the same manner as polystyrene tubes to firmly bond organo-chemical and biologic materials having amino groups capable of coupling.

EXAMPLE 6

Polystyrene balls of 6.4 mm coated with a synthetic polypeptide (p-Phe-Lys, molecular weight, 30,000) are activated with a 0.5% aqueous solution of pentane-1,5-dial. The resultant balls are mixed at pH 7.5–8.5 in a 0.05 moles/l phosphate buffer with a purified $T_3$ antibody. The $T_3$ antibody was raised in rabbit by using a $T_3$ bovine serum albumin conjugate as immunogen, prepared with 1-ethyl-3-(dimethyl-aminopropyl)carbodiimide (EDAC). The Schiff bases formed were reduced in some cases precautionarily with sodium borohydride, but a substantial difference in the stability was not manifested. The remaining active groups were saturated with bovine serum albumin. The saturation was complete in most cases only after several days; saturation was monitored by measuring the non-specific linkage. The repeatedly washed balls were dried in an air current or stored in a 0.05 moles/l tris/hydrochloric acid buffer with the addition of bovine serum albumin. For reconstitution before use, the dried balls were placed into the same buffer for one hour.

What is claimed is:

1. A process for preactivating a hydrophobic plastic surface for the immobilization of organo-chemical and biologic materials which comprises contacting the plastic surface with a solution or suspension of a polypeptide to form a coating on the plastic surface, said polypeptide comprises a hydrophobic amino acid capable of being adsorbed by the plastic surface and an amino acid having a side chain capable of activation and coupling with said organo-chemical and biologic materials, and washing the thus coated surface.

2. A process according to claim 1, wherein the biological material is an antibody or an antigen.

3. A process according to claim 1 wherein the polypeptide is a phenylalanine-lysine copolymer.

4. A preactivated plastic surface for the immobilization of organo-chemical and biologic materials prepared by coating a hydrophobic plastic surface with a polypeptide comprising a hydrophobic amino acid capable of being adsorbed by the plastic surface and an amino acid having a side chain capable of activation and coupling with said organo-chemical and biologic materials.

5. A preactivated plastic surface according to claim 4, wherein the hydrophobic amino acid is phenylalanine, valine or leucine.

6. A preactivated plastic surface according to claim 4, wherein the amino acid having a side chain capable of activation and coupling is lysine, arginine, ornithine, cysteine, glutamic acid, threonine or serine or aspartic acid.

7. A preactivated plastic surface according to claim 4, wherein the surface is coated with a phenylalanine-lysine copolymer.

8. A preactivated surface according to claim 7, wherein the ratio of hydrophobic amino acid to amino acid having a side chain is 1:1.

9. A preactivated plastic surface according to claim 4, wherein the polypeptide has a molecular weight above 10,000.

* * * * *